United States Patent
Keeping et al.

(10) Patent No.: US 7,066,336 B2
(45) Date of Patent: Jun. 27, 2006

(54) MICRO-FILTRATION

(75) Inventors: Sean Crispian Keeping, Shortlands (GB); Dieter Binz, Ladenburg (DE); Colin Ernest Howell, St. Neots (GB); Leslie Jamson, Cheltenham (GB); Robert Arthur Mead, Huntingdon (GB); Charles Lucas Greensted, Cheltenham (GB); David Edward Coe, St. Neots (GB)

(73) Assignee: ABB Limited, Staffordshire (GB)

( * ) Notice: Subject to any disclaimer, the term of this patent is extended or adjusted under 35 U.S.C. 154(b) by 624 days.

(21) Appl. No.: 09/867,743

(22) Filed: May 31, 2001

(65) Prior Publication Data

US 2002/0179543 A1 Dec. 5, 2002

(51) Int. Cl.
*C02F 1/00* (2006.01)

(52) U.S. Cl. .............. 210/359; 210/387; 210/411; 210/416.1; 210/798

(58) Field of Classification Search .............. 210/359, 210/387, 411, 416.1, 798
See application file for complete search history.

(56) References Cited

U.S. PATENT DOCUMENTS

| 3,392,835 | A | | 7/1968 | Asper | |
|---|---|---|---|---|---|
| 4,039,450 | A | * | 8/1977 | Brown | 210/400 |
| 4,260,496 | A | * | 4/1981 | Beer | 210/780 |
| 4,752,386 | A | | 6/1988 | Schulz | |
| 4,861,688 | A | * | 8/1989 | Miura et al. | 210/770 |
| 5,439,598 | A | * | 8/1995 | Clough | 210/770 |
| 2002/0179543 | A1 | * | 12/2002 | Keeping et al. | 210/798 |

FOREIGN PATENT DOCUMENTS

GB     2196269 A     4/1988

* cited by examiner

*Primary Examiner*—Robert James Popovics
*Assistant Examiner*—T. Woodruff
(74) *Attorney, Agent, or Firm*—Larson & Taylor, PLC

(57) ABSTRACT

A filter assembly for ultra-filtration of fluids such as waste water comprises a porous tube which is incrementally advanced into the fluid so as to expose a fresh portion periodically and maintain a flow rate over a period of time.

8 Claims, 5 Drawing Sheets

MICRO-FILTRATION

The present invention relates to the filtration of a contaminated fluid, particularly waste water, to produce a liquid sample substantially free of solid particles. The invention is concerned with the problem of obtaining a filtrate over a prolonged period of time, avoiding the problems of filter clogging.

Prior art materials and membranes suitable for ultra filtration exists. However, such materials tend to get clogged in use, and cannot be used continuously over a prolonged period of time, for example over a period of weeks or even months.

Ultra filtration arrangements for filtering particulates out of air are known. However, such arrangements are generally not suitable for immersion in a liquid and cannot be applied to treatment of waste water.

The present invention is particularly applicable to the analysis of waste water, where the water content is unpredictable, and the filter must be left with minimal maintenance for a period of several months. Conventional filter assemblies would not function reliably in such an environment.

In a first aspect, the invention provides a method of operating a filter assembly comprising:
  providing a filter assembly having a portion of filter element, preferably comprising an elongate porous tube, exposed to a fluid to be filtered;
  drawing fluid through the filter element, thereby permitting the filter element to become at least particularly clogged with particles in the fluid;
  periodically exposing a further portion of the filter element surface;
  drawing further fluid through the filter element.

Preferably, exposing a portion of the filter element comprises incrementally advancing the filter element into the fluid to be filtered.

Preferably the filter element comprises a substantially cylindrical tube, Preferably, exposing a further portion of the filter element surface comprises incrementally advancing the tube out of a housing.

The filter element may be advanced by means of a relatively rotatable threaded shaft or screw and nut member, one of the screw or shaft preferably being arranged to be rotated by a motor.

When the working surface of filter has been fully exposed, the filter element may be replaced. The interval between element replacements may be increased and the reliability of fluid flow during such intervals may be improved by means of the invention.

Periodic back-flushing of the filter element may be employed to reduce clogging further.

In a further aspect, the invention provides a filter assembly comprising an elongate porous tubular filter element having a portion arranged to be exposed to a fluid to be filtered and means for incrementally exposing a further portion of the filter element as the filter becomes clogged.

The apparatus preferably also includes means for drawing fluid through the filter element, preferably comprising pump means, preferably a peristaltic pump.

In a highly advantageous development, the assembly is arranged so that a single drive means is arranged to operate the pump means to draw fluid through the filter element and to advance the filter element to expose further portions of the surface. Such a combination can significantly reduce the cost, weight, complexity and size of the assembly.

In an advantageous embodiment, the assembly includes coupling means arranged to couple a rotary drive to the pump means to draw fluid through the filter element when rotation is applied in a first direction and to advance the filter element when rotation is applied in the opposite direction. The coupling may include a unidirectional clutch coupling an input shaft to means for advancing the filter element, for example a screw drive mechanism.

Most advantageously, the pump is arranged to pump fluid back through the filter element when rotated in the second direction. This can effect back-flushing of the filter element and reduce clogging. This may be achieved effectively using a peristaltic pump.

The filter element is preferably disposable. Preferably, the filter assembly is removably coupled to a drive means, for example a motor, so that the filter assembly may be renewed without having to renew the drive motor. The filter assembly may be mounted in a cartridge as described in our concurrently filed application Ser. No. 09/867,741, the entire disclosure of which is incorporated herein by reference. In such a case, the filter assembly may be located on the cartridge and the drive motor on the main analysis unit.

The invention is particularly applicable to the filtering of liquids (rather than gases), particularly fluids such as contaminated water.

An embodiment of the invention will now be described, by way of example only, with reference to the accompanying drawings in which:-

FIG. 1 schematically depicts a pump and filter arrangement according to an embodiment;

Figure 1:
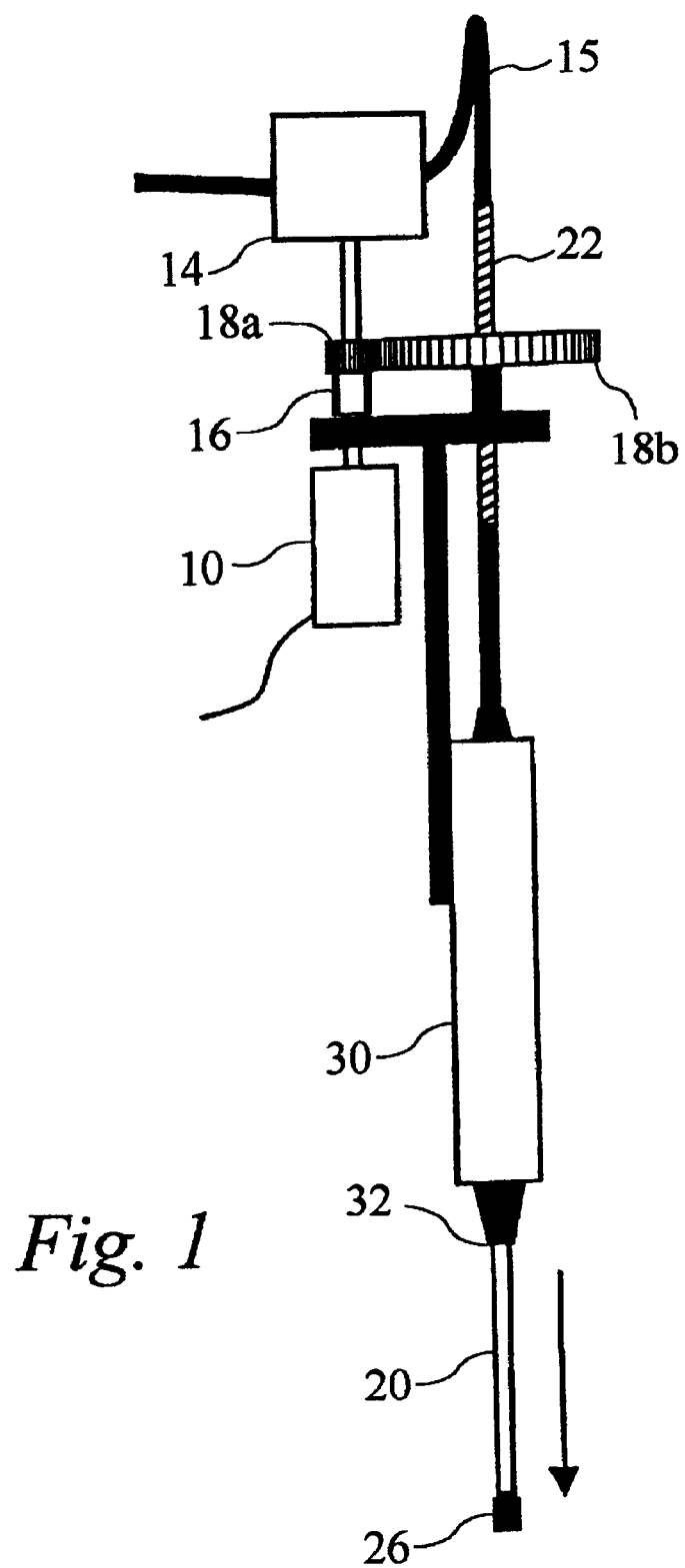

Referring to FIG. 1, a drive motor 10, typically a stepper motor, is arranged to drive a pump 14, typically a peristaltic pump, which draws fluid through a filter element 20 via tube 15. The drive mechanism 10 also serves to advance the filter element 20 by means of drive shaft 22, as will be explained in greater detail below.

Figure 2:
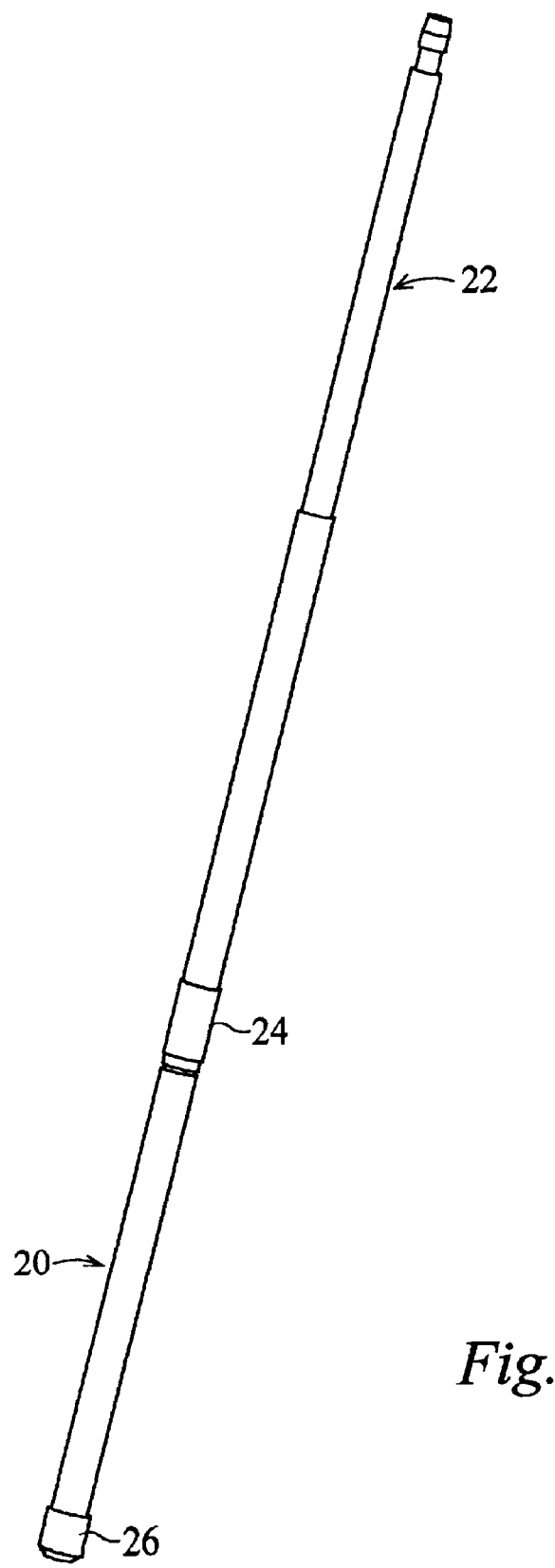
FIG. 2 shows a filter element and drive tube for use in the embodiment of FIG. 1 in greater detail.
Figure 3:
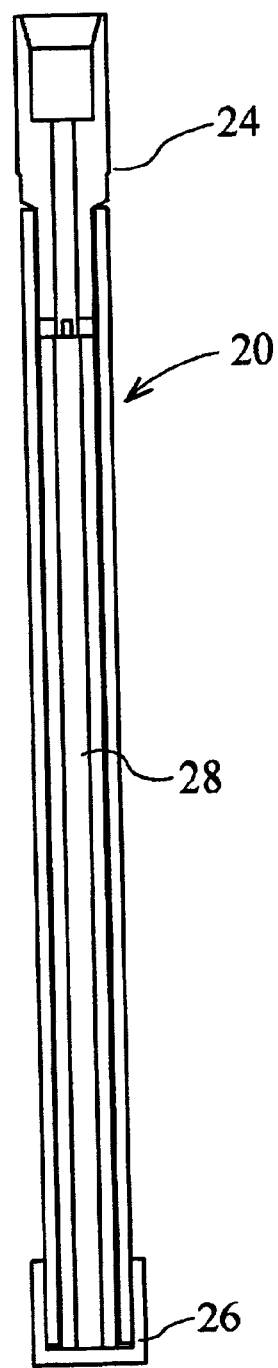
FIGS. 3 and 4 are exploded views showing greater detail of the mounting of the filter tube, FIG. 4 with the filter tube removed.
Figure 4:
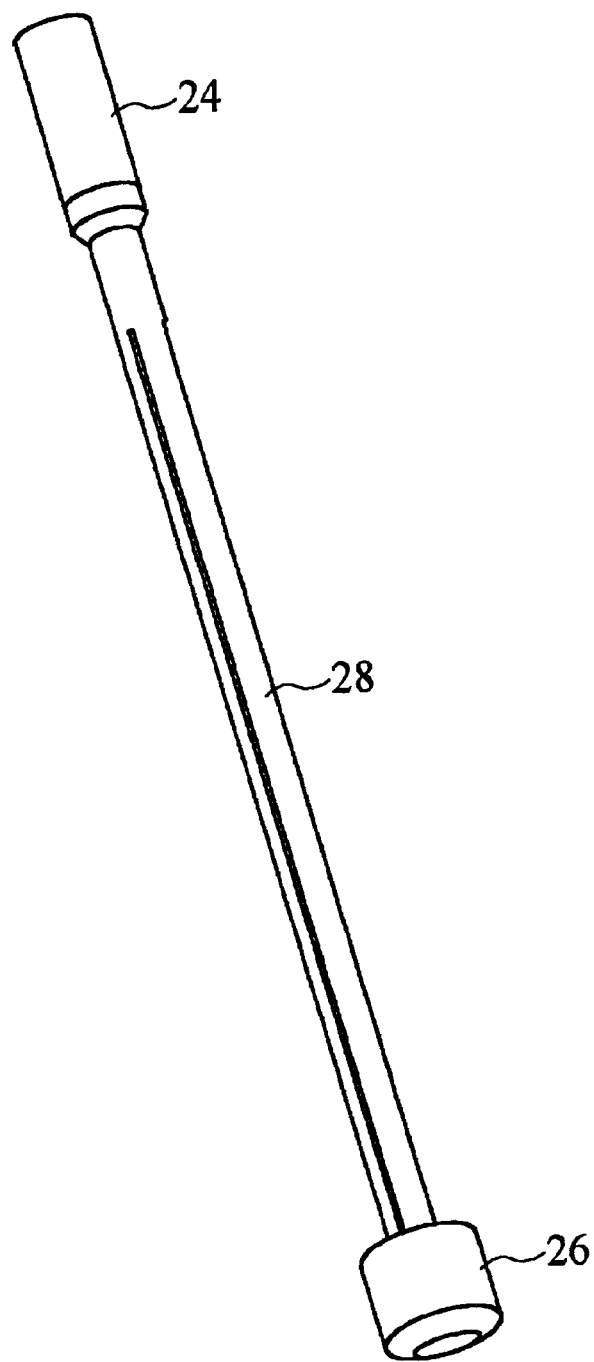

Referring now to FIGS. 2 to 4, the construction of the filter element assembly will be described in greater detail.

The filter element 20 comprises a porous tube of a commercially available filter material having an appropriate pore size. The pore size will typically be chosen for ultra-filtration, for example to exclude bacteria and larger particulates, typically less than 0.4 microns, more typically of the order of 0.2 microns.

Known commercially available filter tubes designed for use in static filter assemblies are cylindrical, but the tube need not necessarily be so and other shapes may be used. We have considered modifications in which filter structures other than tubes could be gradually exposed and such modifications are not ruled out. Indeed, superficially, it may appear simpler to provide an arrangement for advancing a relatively flat filter element. However, we have found that a tube has the benefits that it can provide a large surface area in a compact structure, and can also provide a defined channel for ready connection to a pump. Furthermore, we have found that, surprisingly, more reliable results may be obtained over a prolonged period of time, particularly in polluted water environments, if a tube is advanced out of a housing.

The filter element is preferably supplied sterile, and may be pre-filled with a sterilising solution (this can be flushed out prior to use) to maintain a sterile environment within the filter assembly.

The (delicate) porous filter tube is supported between an upper coupling member 24 and end cap 26 which helps retain the element and protect the end. As can best be seen from FIGS. 3 and 4 (in the latter of which the filter element 20 is not shown), an inner grooved tube 28 provides mechanical rigidity to the porous element, the grooves allowing fluid drawn through the element to pass into a bore from which the fluid can pass to the pump 12.

The operation of the assembly will now be explained.

The drive shaft 22 is threaded and is mounted in a complementary threaded nut driven by gear wheel 18b located around the drive shaft. The nut is mounted so that it cannot move axially but can rotate freely. The gear 18b is driven by gear 18a mounted on uni-directional clutch 16 (which may be of conventional design). The drive shaft is rotated by the stepper motor 10, which also drives the pump 14.

When the motor rotates the drive shaft in a first direction (for example clockwise when viewed from below), the unidirectional clutch 16 slips freely and hence the gear wheels 18a and 18b remain stationary. The result is that the filter element is not translated axially but the rotation causes the pump 14 to operate to draw fluid through the filter element. This corresponds to normal operation.

Periodically, the direction of rotation is reversed. This causes the unidirectional clutch 16 to engage thereby causing the gear wheels 18a, 18b to be driven. The nut within gear wheel 18b rotates but the drive shaft 22 is prevented from rotating by suitable means, for example a projecting pin which can slide axially in a groove but not turn. The relative rotation causes the drive shaft 22 and hence filter 20 to be axially advanced. It also causes the pump 14 to pump in reverse, thereby back-flushing the filter. The amount and number of rotations are chosen to ensure an appropriate rate of exposure of the filter element, for example so that the filter is exposed over the course of a month.

Figure 5B:
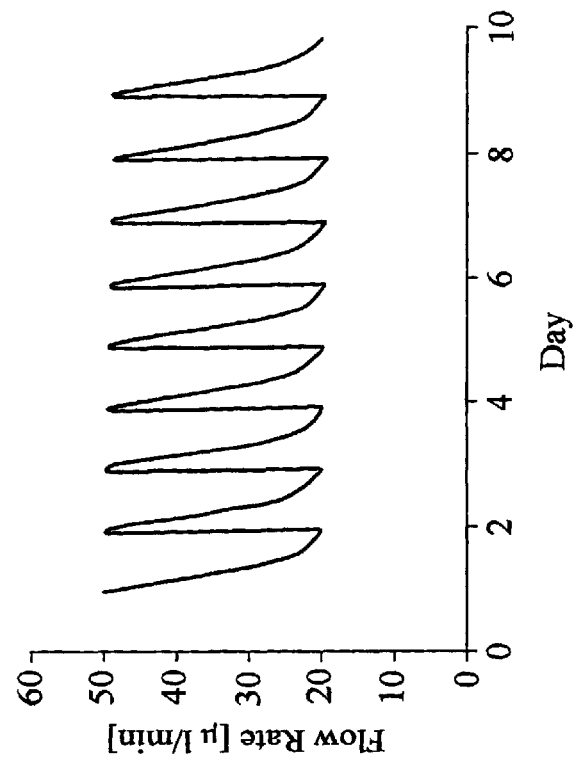
FIG. 5 shows a comparison of typical results obtained with a test filter.
Figure 5A:
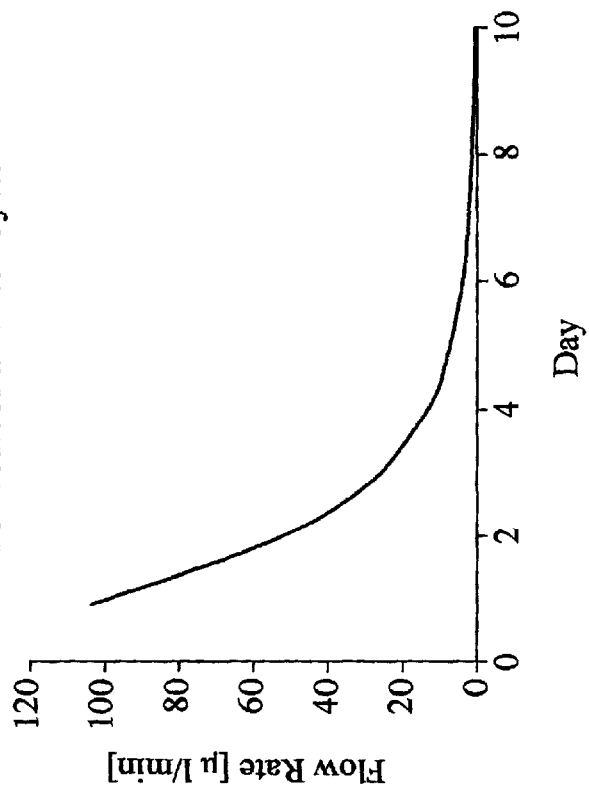

FIG. 5 shows a comparison of typical results obtained with (a) a simple arrangement using a filter tube continually exposed to fluid and (b) the same tube advanced by means of the above embodiment in a simulation of waste water conditions. The conditions were chosen to correspond to highly contaminated water and a minimum acceptable flow rate of 20 μl/min.

It can be seen that the tube alone gave a high initial flow rate, due to the greater surface area exposed to the fluid, but by before the fourth day the initial rate had dropped from over 100 μl/min to below 20 μl/min and thereafter tailed off to virtually no flow. The filter would therefore have to be replaced approximately every 3 days. In addition, the high initial flow rate may present problems as the surplus filtrate would have to be exhausted.

Normally the filter is advanced at a rate sufficient to ensure adequate flow at all times under worst-case conditions; this gives a constant rate of advance and a known filter life. A typical advance rate of the order of 1 mm a day will give a life of 30 days for a 3 cm length of tube, which means that, in practice, a filter tube of about 4–5 cm in length can be changed monthly with some filter in reserve and for mounting. Filter advance rates may typically vary from about 0.1 mm/day to about 1 cm/day, depending on the filter size, flow rate required and expected fluid conditions; higher flow rates and higher levels of pollution will increase necessary filter advance rates in order to maintain flow, and will consequently lead to shorter operating life for a given filter size.

In a development, it is possible to obtain a measure of flow through the filter, or to detect a fall in flow rate below a predetermined threshold and to advance the filter element based on the measure or detection. Detection may be provided by, for example, a pressure or level sensor coupled to a reservoir located in a fluid path from pump 14 to other analysis equipment. Normally the reservoir will be full and overflowing (to ensure that the sample does not stagnate in the reservoir). As soon as the pump 14 fails to deliver fluid at a rate matching the rate required by the analysis equipment, a drop in pressure or level in the reservoir (or overflow) will be detectable and this can be used to trigger advancing of the filter. This may increase filter life (in less polluted environments), although the filter will still normally be replaced at regular intervals, and ensure a more even fluid flow.

Modifications of detail are possible within the scope of the invention and the invention is not to be construed as limited to the embodiments described. Features described herein may be provided independently, unless otherwise stated.

What is claimed is:

1. A filter assembly for obtaining a sample of filtrate from a contaminated fluid, the assembly comprising a filter element comprising an elongate porous tube having an exterior surface wherein a portion of the exterior surface is arranged to be immersed in a fluid to be filtered and wherein the tube is substantially rigid so that, in use, the interior bore is maintained as a passage for the filtered fluid; and a pump, having an inlet and coupled to the interior bore of the filter element and an outlet, for drawing filtrate through the filter element from the exterior surface of the filter element to the interior bore and through the interior bore to the inlet of the pump;

means for incrementally extending a further portion of the exterior surface of the filter element to immerse the further portion in the contaminated fluid as the filter element becomes clogged.

2. Apparatus according to claim 1 wherein a single drive means is arranged to operate the pump to draw fluid through the filter element and to advance the filter element to expose further portions of the surface.

3. Apparatus according to claim 1 wherein the assembly includes coupling means arranged to couple a rotary drive to the pump to draw fluid through the filter element when rotation is applied in a first direction and to advance the filter element when rotation is applied in the opposite direction.

4. Apparatus according to claim 1 wherein the pump is arranged to pump fluid back through the filter element from the interior surface of the filter element to the exterior surface of the filter element to effect back-flushing of the filter element.

5. Apparatus according to claim 1 wherein the filter assembly is removably coupled to a drive means so that the filter assembly may be renewed without having to renew the drive means.

6. Apparatus according to claim 1 wherein the filter element comprises a substantially cylindrical tube.

7. Apparatus according to claim 1 wherein the further portion of the exterior surface of the filter element is incrementally exposed by means of a relatively rotatable threaded shaft or screw and nut member, one of the screw or shaft being arranged to be rotated by drive means.

8. A filter assembly for obtaining a sample of filtrate from a contaminated fluid, the assembly comprising:

a filter element comprising an elongate porous tube having an exterior surface wherein a portion of the exterior surface is arranged to be exposed to a fluid to be filter; and means for incrementally exposing a further portion of the exterior surface of the filter element to the contaminated fluid as the filter element becomes clogged;

the interior bore of the tube being arranged to couple to an inlet of a pump for drawing filtrate through the filter element from the exterior surface of the filter element to the interior bore of the filter element;

a single drive means being arranged to operate the pump to draw fluid through the filter element and to advance the filter element to expose further portions of the surface; and the filter assembly further including coupling means arranged to couple a rotary drive to the pump to draw fluid through the filter element when rotation is applied in a first direction and to advance the filter element when rotation is applied in the opposite direction.

* * * * *